United States Patent
Morimoto

(10) Patent No.: US 10,772,486 B2
(45) Date of Patent: Sep. 15, 2020

(54) ENDOSCOPE

(71) Applicant: FUJIFILM Corporation, Tokyo (JP)

(72) Inventor: Yasuhiko Morimoto, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 15/298,243

(22) Filed: Oct. 20, 2016

(65) Prior Publication Data

US 2017/0112363 A1 Apr. 27, 2017

(30) Foreign Application Priority Data

Oct. 23, 2015 (JP) ................. 2015-209125

(51) Int. Cl.
| | |
|---|---|
| A61B 1/00 | (2006.01) |
| A61B 1/018 | (2006.01) |
| A61B 1/06 | (2006.01) |
| A61B 1/12 | (2006.01) |
| A61B 8/12 | (2006.01) |
| A61B 8/00 | (2006.01) |

(52) U.S. Cl.
CPC ......... *A61B 1/00098* (2013.01); *A61B 1/018* (2013.01); *A61B 1/0676* (2013.01); *A61B 1/12* (2013.01); *A61B 8/12* (2013.01); *A61B 8/445* (2013.01); *A61B 1/122* (2013.01)

(58) Field of Classification Search
CPC ... A61B 1/00098; A61B 1/018; A61B 1/0676; A61B 1/12; A61B 1/0008; A61B 8/12; A61B 8/445; A61B 8/122; A61B 1/122; A61B 1/012; A61B 1/0125; A61B 1/00064; A61B 1/00071; A61B 1/005; A61B 1/0051; A61B 1/04; A61B 1/05; A61B 1/0661

USPC ......... 600/104, 106–107, 113–114, 127, 129
See application file for complete search history.

(56) References Cited

U.S. PATENT DOCUMENTS

| | | | |
|---|---|---|---|
| 2002/0091303 A1* | 7/2002 | Ootawara | A61B 1/00098 600/106 |
| 2015/0173711 A1* | 6/2015 | Hiraoka | A61B 8/445 600/466 |

FOREIGN PATENT DOCUMENTS

| | | |
|---|---|---|
| DE | 19714950 | 10/1997 |
| JP | S5910968 | 4/1984 |
| JP | H04314439 | 11/1992 |

(Continued)

OTHER PUBLICATIONS

English Translation of JP2013183964A provided by Espacenet (Year: 2013).*

(Continued)

*Primary Examiner* — Ryan N Henderson
*Assistant Examiner* — Pamela F Wu
(74) *Attorney, Agent, or Firm* — JCIPRNET

(57) ABSTRACT

An elevator provided in a treatment tool leading section of a leading end section of the endoscope includes a wide body portion that is provided on a distal end side with respect to a rotation shaft, and has a width more than that of a narrow body portion provided on a proximal end side. The wide body portion projects through an opening in an upper portion in an elevator accommodation groove in a state where the elevator rises most. The wide body portion prevents the treatment tool from dropping into a gap in a side when the elevator is lying. Meanwhile, when the elevator is cleaned with a cleaning brush, raising the elevator enables side faces of the elevator to be easily cleaned.

27 Claims, 16 Drawing Sheets

(56) References Cited

FOREIGN PATENT DOCUMENTS

| JP | 2000000208 | | 1/2000 | |
|---|---|---|---|---|
| JP | 2000051145 | | 2/2000 | |
| JP | 2000175864 | | 6/2000 | |
| JP | 2013-183964 | | 9/2013 | |
| JP | 2013183964 A | * | 9/2013 | ......... A61B 1/00098 |
| WO | 2015107801 | | 7/2015 | |

OTHER PUBLICATIONS

"Search Report of Europe Counterpart Application", dated Mar. 6, 2017, p. 1-p. 8.
Office Action of Japan Counterpart Application, with English translation thereof, dated Nov. 26, 2018, pp. 1-6.
Office Action of China Counterpart Application, with English translation thereof, dated Aug. 21, 2019, pp. 1-13.

* cited by examiner

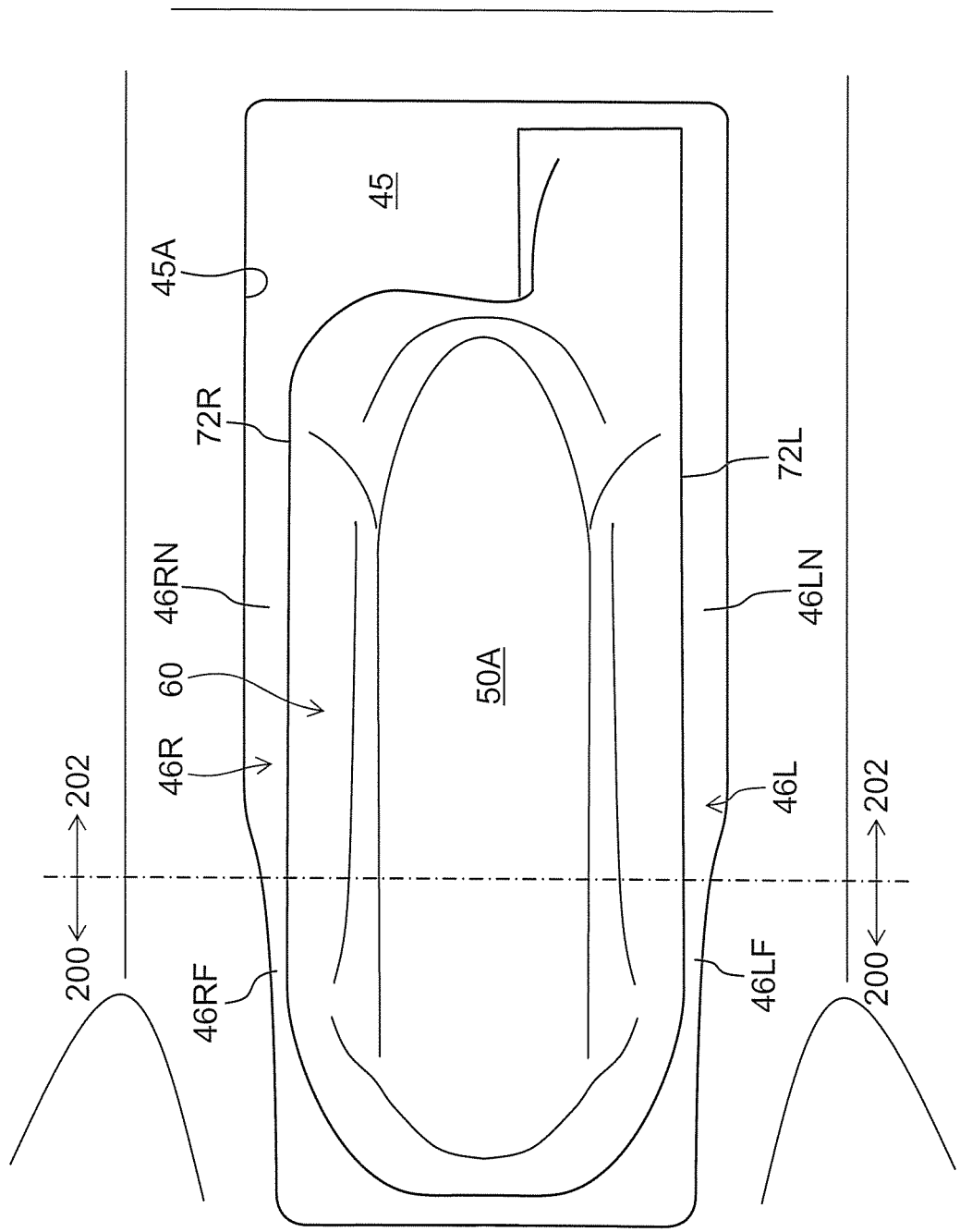

ENDOSCOPE

CROSS-REFERENCE TO RELATED APPLICATIONS

The present application claims priority under 35 U.S.C. § 119 to Japanese Patent Application No. 2015-209125, filed on Oct. 23, 2015. The above application is hereby expressly incorporated by reference, in its entirety, into the present application.

BACKGROUND OF THE INVENTION

Field of the Invention

The present invention relates to an endoscope, and more particularly to an endoscope including an insertion section whose leading end is provided with a treatment tool elevator (hereinafter referred to simply as an elevator) that controls a leading direction of a treatment tool.

Description of the Related Art

In conventional endoscopes, there are known an ultrasound endoscope and a side-viewing endoscope each of which includes a treatment tool leading section through which various treatment tools inserted from a treatment tool inlet provided in an operation section lead out from their leading ends, and an elevator provided in the treatment tool leading section to control a leading direction of a treatment tool.

Japanese Patent Application Laid-Open No. 2013-183964 (Patent Literature 1) provides a treatment tool leading section that includes an elevator whose leading end is widened to reduce a gap portion where an operation wire for driving an elevator is disposed to prevent a treatment tool from dropping into a side of the elevator, or the gap portion.

Conventionally, a cleaning brush is used to clean the treatment tool leading section provided with the elevator, and thus if a gap portion on a side of the elevator (particularly a leading end thereof) in the treatment tool leading section is reduced as described in Patent Literature 1 to prevent the treatment tool from dropping into the gap portion, bristles of the cleaning brush also tend to be difficult to enter the gap portion. In Patent Literature 1, even if a raising angle of the elevator is changed, a size of the gap portion on a side of the elevator as well as easiness of cleaning does not change because the whole of the elevator is buried in a recessed portion. Thus, there is a problem of requiring time and effort for cleaning operation.

The present invention is made in light of the above-mentioned circumstances, and has an object to provide an endoscope capable of reducing time and effort required for cleaning operation of an elevator.

SUMMARY OF THE INVENTION

To achieve the object described above, an endoscope in accordance with an aspect of the present invention includes: an insertion section having a leading end and a base end; an operation section provided at the base end of the insertion section; a leading end body provided at the leading end of the insertion section; an elevator accommodation groove provided in the leading end body, the groove having an opening in a side face of the leading end body; a treatment tool insertion channel provided in the insertion section, the channel communicating with the elevator accommodation groove; and a treatment tool elevator provided in the elevator accommodation groove to be rotatable around a rotation axis in a direction including a component of a direction orthogonal to a longitudinal axis of the insertion section, the base guiding a treatment tool led through the treatment tool insertion channel. In the endoscope, the treatment tool elevator has a proximal end portion, a distal end portion with a radial distance from the rotation axis more than a radial distance to the proximal end portion from the rotation axis, a treatment tool guiding face provided between the proximal end portion and the distal end portion, and an elevator side face adjacent to the treatment tool guiding face, the side face having a direction including an axial component of the rotation axis, the direction being a normal direction. The elevator accommodation groove has an elevator accommodation groove side face facing the elevator side face across a gap portion. In a state where the treatment tool elevator is lying, the gap portion has: a narrow gap portion formed between a distal end portion side face positioned on a distal end portion side in the elevator side face, and the elevator accommodation groove side face; and a wide gap portion formed between a proximal end portion side face closer to the proximal end portion than the distal end portion side face in the elevator side face, and the elevator accommodation groove side face, the wide gap portion being wider axially than the narrow gap portion. In a state where the treatment tool elevator rises, the distal end portion side face projects outside from the opening of the elevator accommodation groove.

According to the present aspect, in a state where the elevator is lying, the narrow gap portion is provided between the distal end portion side face of the elevator, and elevator accommodation groove side face to prevent a treatment tool from dropping into the gap portion from the elevator. When the elevator rises, the distal end portion side face of the elevator projects outside from the opening of the elevator accommodation groove to allow also the distal end portion side face of the elevator, adjacent to the narrow gap portion, to be easily cleaned by using a cleaning brush.

In another aspect of the present invention, the treatment tool elevator may include a wide body portion that projects outside from the opening of the elevator accommodation groove when the treatment tool elevator provided on the distal end portion side rises, and a narrow body portion that is provided closer to the proximal end portion than the wide body portion, and is narrower axially than the wide body portion.

In yet another aspect of the present invention, the wide body portion may have a longitudinal section with a rounded shape with respect to an axial direction of the wide body portion.

In yet another aspect of the present invention, the wide body portion may have a cross section with a rounded shape with respect to the axial direction of the wide body portion.

In yet another aspect of the present invention, in a state where the treatment tool elevator is lying, the elevator accommodation groove may include a narrow groove that is provided on the distal end portion side, and a wide groove that is provided closer to the proximal end portion than the narrow groove and is wider axially than the narrow groove.

In yet another aspect of the present invention, the elevator accommodation groove may include a leading portion that increases in axial width toward the opening.

In yet another aspect of the present invention, the leading portion may be an edge of the elevator accommodation groove on an opening side, the edge having a cross section with a rounded shape.

In yet another aspect of the present invention, a back face of the treatment tool elevator, the back face being opposite to the treatment tool guiding face, may have a longitudinal section with a rounded shape with respect to the axial direction.

In yet another aspect of the present invention, the endoscope may include a raising lever that is provided in the leading end body and is coupled to the treatment tool elevator to turn the treatment tool elevator around the rotation axis, and a transfer member that is provided from the operation section to the leading end body through the insertion section and transfers displacement generated in the operation section to the raising lever.

According to the present invention, time and effort required for cleaning operation of the elevator can be reduced.

BRIEF DESCRIPTION OF THE DRAWINGS

FIG. 16 is a top view illustrating a peripheral portion of the elevator in another embodiment in a state where the elevator is lying.

DETAILED DESCRIPTION OF THE PREFERRED EMBODIMENTS

Hereinafter, preferable embodiments of the present invention will be described in detail with reference to accompanying drawings.

Figure 1:
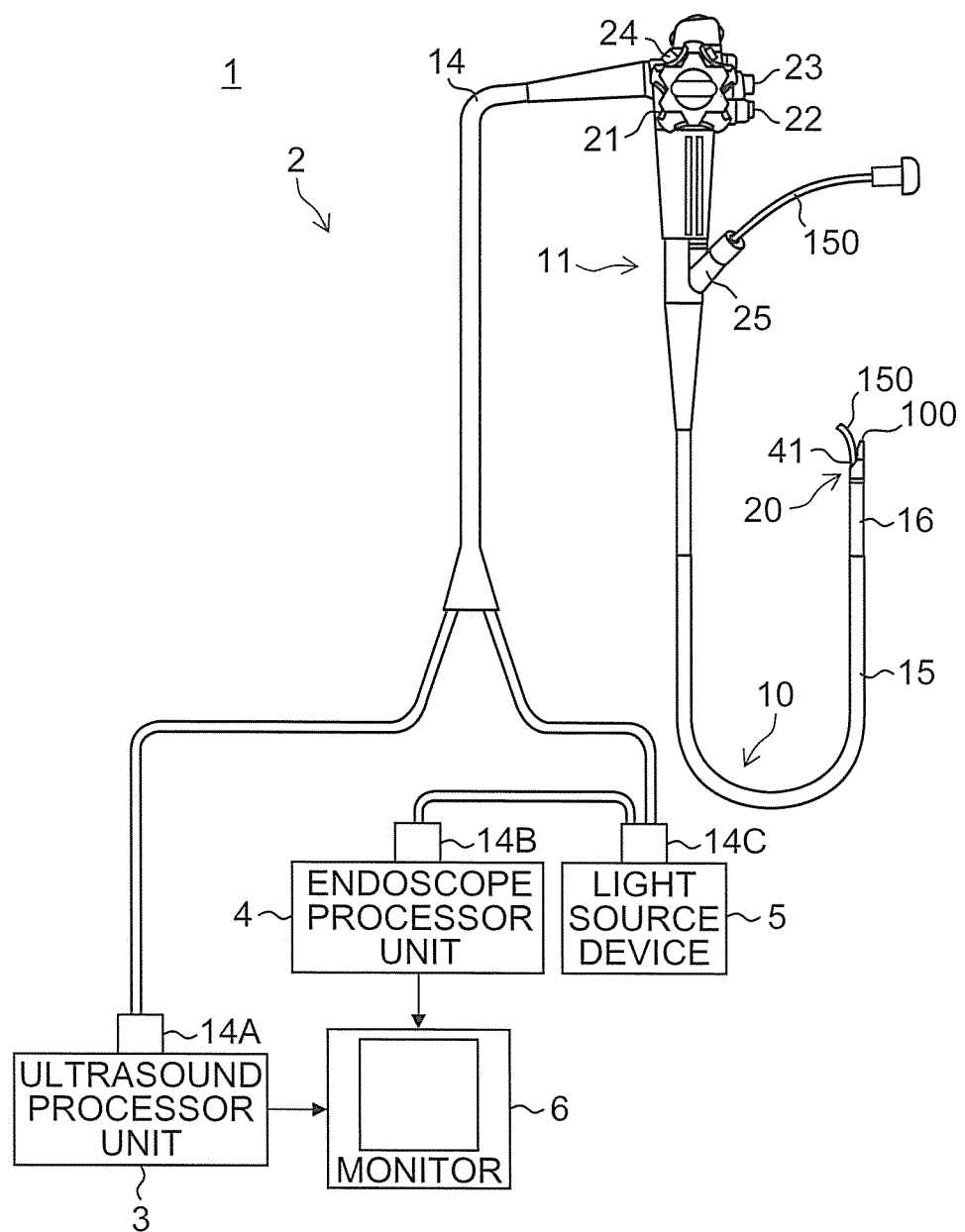
FIG. 1 is a general structural view of an ultrasound inspection system including an ultrasound endoscope to which the present invention is applied.

FIG. 1 is a general structural view of an ultrasound inspection system 1.

The ultrasound inspection system 1 includes an ultrasound endoscope 2 that takes an endoscope image and an ultrasound image in the body, an ultrasound processor unit 3 that generates the ultrasound image, an endoscope processor unit 4 that generates the endoscope image, a light source device 5 that supplies illumination light to the ultrasound endoscope 2 to illuminate the inside of the body, and a monitor 6 that displays the endoscope image and the ultrasound image.

The ultrasound endoscope 2 is a convex type ultrasound endoscope, and includes an insertion section 10 to be inserted into the body, the insertion section 10 having a leading end and a base end, an operation section 11 provided at the base end of the insertion section 10, and a universal cord 14 whose base end is connected to the operation section 11. The universal cord 14 is provided at its leading end with connectors 14A, 14B, and 14C to connect the ultrasound endoscope 2 to the ultrasound processor unit 3, the endoscope processor unit 4, and the light source device 5, respectively.

The insertion section 10 includes a flexible portion 15, a curvature portion 16, and a leading end section 20, which are provided in the order from the base end to the leading end.

The flexible portion 15 has flexibility to curve in any direction along an insertion route of the insertion section 10. The curvature portion 16 curves in each of directions of up and down, and right and left, by operating an angle knob 21 of the operation section 11.

The leading end section 20 is provided at its leading end with an ultrasound observation section 100 that receives and transmits ultrasound, and converts received ultrasound into an ultrasound signal being an electric signal to output the ultrasound signal. The ultrasound signal outputted by the ultrasound observation section 100 is transmitted to the ultrasound processor unit 3 connected through the universal cord 14. Then, the ultrasound processor unit 3 generates a tomographic image, as an ultrasound image, of cellular tissue existing in a depth direction of a body wall portion irradiated with ultrasound.

In addition, the leading end section 20 includes an optical observation section that takes an image of an observed site in the body, and an illumination section that irradiates the observed site with illumination light, each of which is provided at a portion closer to the base end than the ultrasound observation section 100. The image taken by the optical observation section is transmitted to the endoscope processor unit 4 connected through the universal cord 14, as an observation image (endoscope image), and the illumination light emitted by the illumination section is propagated from the light source device 5 connected through the universal cord 14 by passing through a light guide in the ultrasound endoscope 2.

Further, the leading end section 20 includes a treatment tool leading section 41 that is provided at a portion closer to the base end than the ultrasound observation section 100. The treatment tool leading section 41 allows a treatment tool 150 inserted into the treatment tool insertion channel in the insertion section 10 from a treatment tool inlet 25 of the operation section 11 to be led outside the insertion section 10. The treatment tool leading section 41 is provided with an elevator 50 described later to adjust a leading direction of the treatment tool 150.

Figure 2:
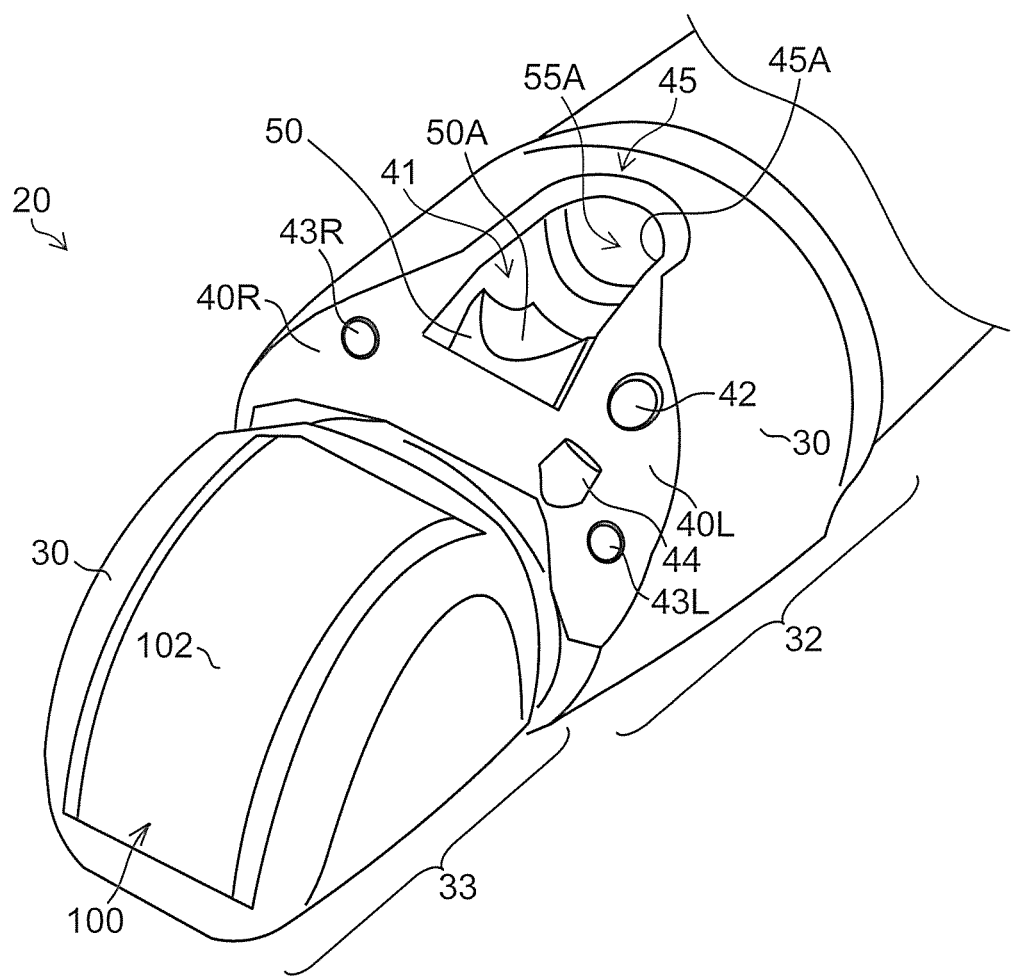
FIG. 2 is a perspective view illustrating a leading end section of the ultrasound endoscope to which the present invention is applied.
Figure 3:
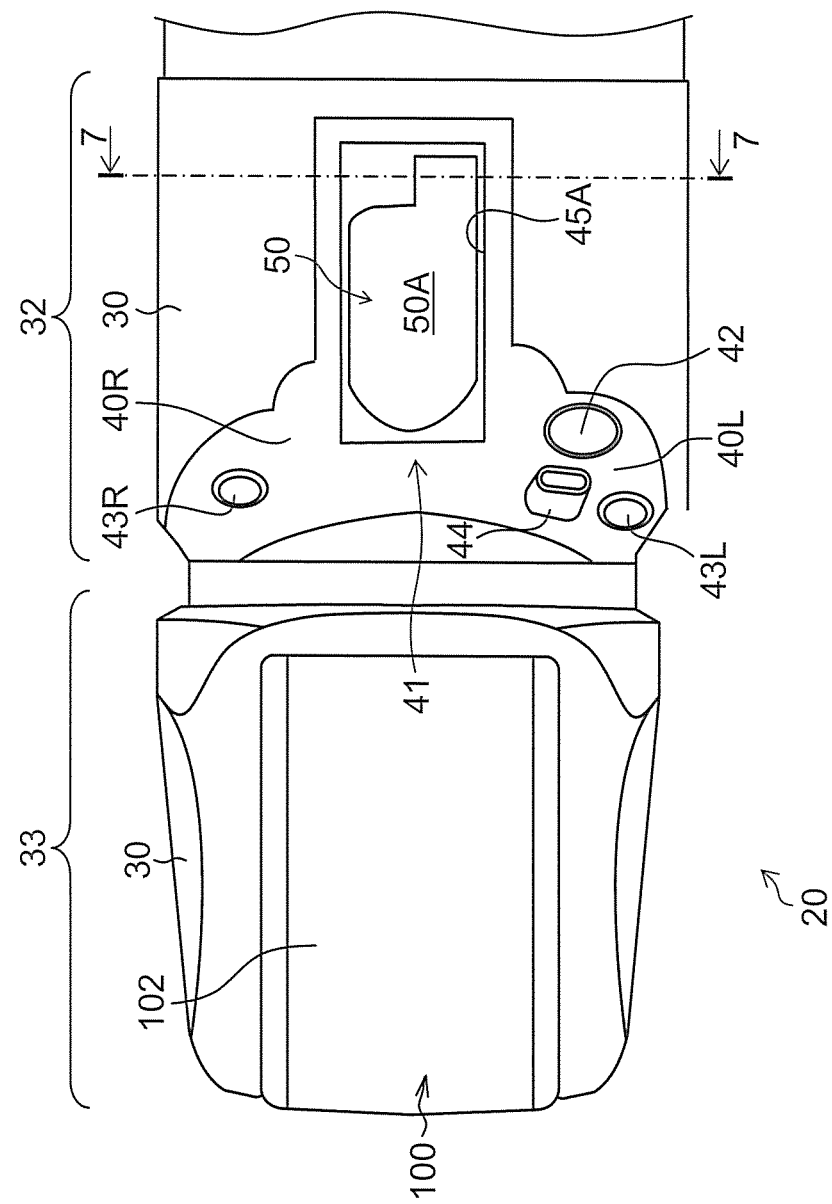
FIG. 3 is a plan view illustrating the leading end section of the ultrasound endoscope to which the present invention is applied.

Next, structure of the leading end section 20 will be described. FIGS. 2 and 3 are a perspective view and a plan view (top view), respectively, illustrating an appearance of the leading end section 20.

The leading end section 20 includes a leading end body 30 that is provided at the leading end of the insertion section 10 to form an outer wall and an inner partition wall of the leading end section 20, a plurality of accommodation sections defined by the leading end body 30, and various components accommodated and held in the accommodation sections.

While detailed description is omitted, a part of the leading end body 30 is detachable as a separate block, and thus each of the components can be assembled in a predetermined accommodation section while the separate block is detached. Attaching the separate block to the leading end body 30 after each of the components is assembled in the corresponding accommodation section allows each of the components to be accommodated and held in the corresponding accommodation section to be fixed to the leading end section 20.

The leading end body 30 is formed of insulating material with insulation, for example, resin material, such as plastic like methacrylate resin and polycarbonate.

The leading end section 20, as illustrated in FIGS. 2 and 3, includes a base section 32 on a base end side, and an extension section 33 extending from the base section 32 to a leading end side.

The extension section 33 is provided with the ultrasound observation section 100 described above on an upper face side of the extension section 33. The ultrasound observation section 100 includes a convex type ultrasound transducer 102 in which a large number of ultrasound vibrators for receiving and transmitting ultrasound are arranged in a convex shape.

When an axial direction of the insertion section 10 is viewed from the base end side of the insertion section 10 to the leading end side thereof, a direction in which the ultrasound observation section 100 and the treatment tool leading section 41 are disposed is referred to as "upper", and a direction opposite to the direction is referred to as "lower", in a direction perpendicular to the axis of the insertion section 10, for terms that indicate up, down, left and right directions.

The base section 32 includes a left inclined face 40L and a right inclined face 40R, extending toward the leading end obliquely upward, and a recessed treatment tool leading section 41 provided in a central portion between the left inclined face 40L and the right inclined face 40R.

The left inclined face 40L includes an observation window 42, an illumination window 43L, and an air-and-water supply nozzle 44. The right inclined face 40R includes an illumination window 43R.

The observation window 42 is provided to acquire an optical image of a subject, and is a component of the optical observation section described above that acquires an image of an observed site as an observation image. In the base section 32 behind the observation window 42, there is accommodated and disposed an imaging system unit that is a component of the optical observation section, and is formed by integrally assembling an imaging optical system and a solid imaging element. The imaging system unit is electrically connected to the endoscope processor unit 4 connected to the universal cord 14.

The illumination windows 43R and 43L each are a component of the illumination section described above that irradiates an observed site with illumination light. In the base section 32 behind the illumination windows 43R and 43L, there is accommodated and disposed a light emission section that is a component of the illumination section, and emits illumination light through the illumination windows 43R and 43L. The light emission section is optically connected to the light source device 5 connected to the universal cord 14, through the light guide.

The air-and-water supply nozzle 44 sprays water and air to the observation window 42 by operating an air-and-water supply button 22 (refer to FIG. 1) of the operation section 11 to perform cleaning of the observation window 42 and the like.

In the treatment tool leading section 41, the elevator 50 is disposed, and an elevator accommodation groove 45 having an opening 45A in a side face (upper side) of the leading end body 30 is formed as a slit-like elevator accommodation space in which the elevator 50 is disposed, the elevator accommodation groove 45 being provided on its base end side with a treatment tool insertion hole 55A.

The treatment tool insertion hole 55A communicates with the treatment tool inlet 25 (refer to FIG. 1) of the operation section 11 through the treatment tool insertion channel (pipe conduit) formed through the inside of the insertion section 10. Thus, the treatment tool inserted from the treatment tool inlet 25 is guided from the treatment tool insertion hole 55A to the elevator accommodation groove 45. Then, the elevator 50 in the elevator accommodation groove 45 bends a leading direction (leading angle) of the treatment tool so that the treatment tool is led toward a side (upper side) of the insertion section 10 from the treatment tool leading section 41.

The treatment tool insertion channel is also coupled to a suction channel, and body fluid or the like is sucked through the treatment tool insertion hole 55A by operating a suction button 23 (refer to FIG. 1) of the operation section 11.

The elevator 50 includes a guide face 50A that is rotatable provided around a rotation axis in an axial direction including a component of a direction orthogonal to a longitudinal axis of the insertion section 10, and that is a treatment tool guiding face for guiding the treatment tool led from the treatment tool insertion channel. The guide face 50A is formed in a concave shape (arc-like shape) in an upper face of the elevator 50 so as to curve upward from a base end side of the leading end section 20 toward a leading end side thereof.

The treatment tool led to the elevator accommodation groove 45 through the treatment tool insertion hole 55A curves upward with respect to an axial direction (longitudinal axis direction of the insertion section 10) of the leading end section 20 along the guide face 50A to be led outside through the opening 45A on an upper side of the elevator accommodation groove 45, the opening 45A being a treatment tool outlet.

Since the elevator 50 is configured to rise and lie by operating a raising operation lever 24 (refer to FIG. 1) of the operation section 11, adjusting a raising angle from a lying state by allowing the elevator 50 to rise or lie enables adjustment of a leading direction (leading angle) of the treatment tool to be led from the treatment tool leading section 41.

Subsequently, there will be described an elevator assembly 49 that supports and drives the elevator 50 in the leading end section 20.

Figure 4:
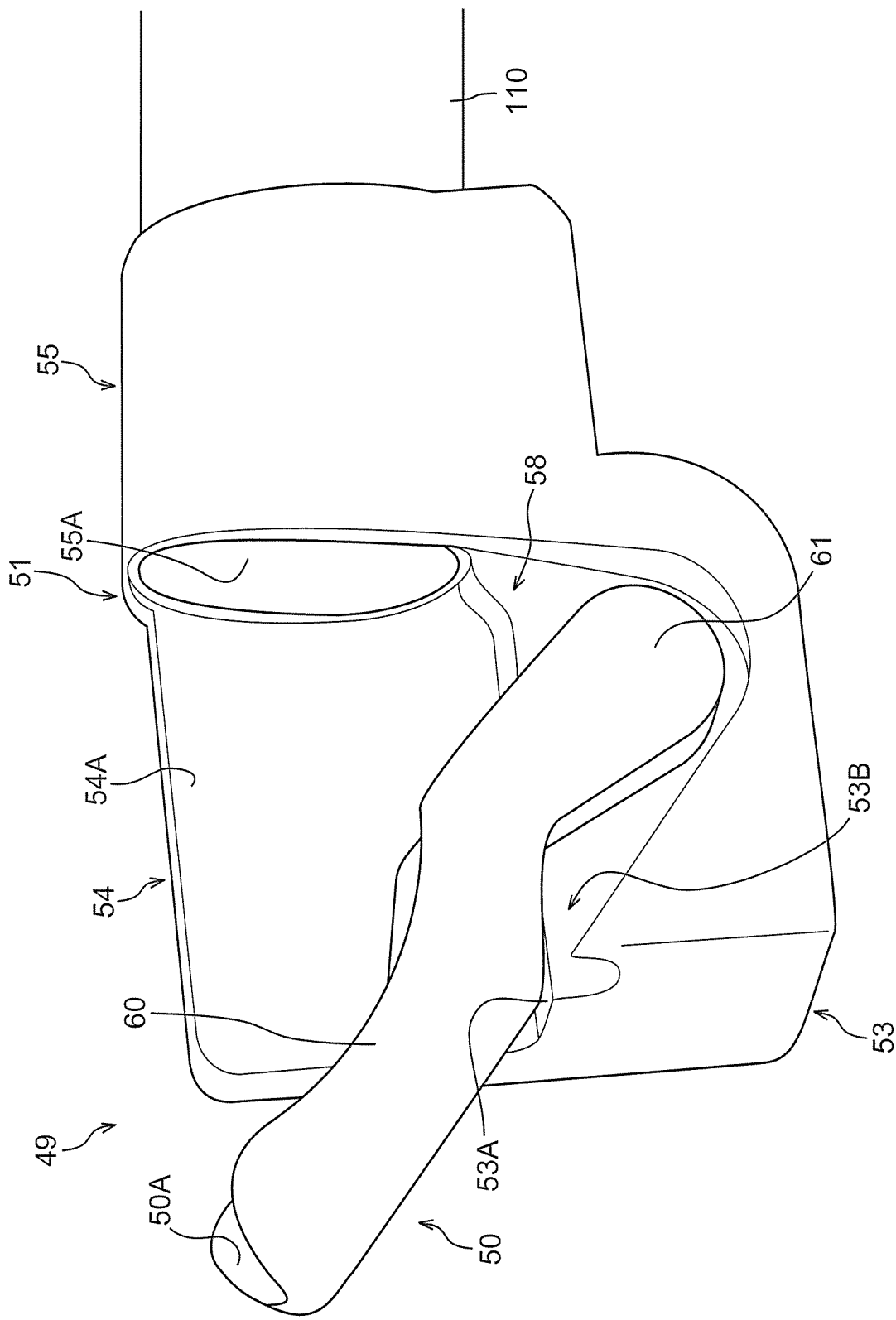
FIG. 4 is a perspective view illustrating the whole of an elevator assembly viewed from the left side.
Figure 5:
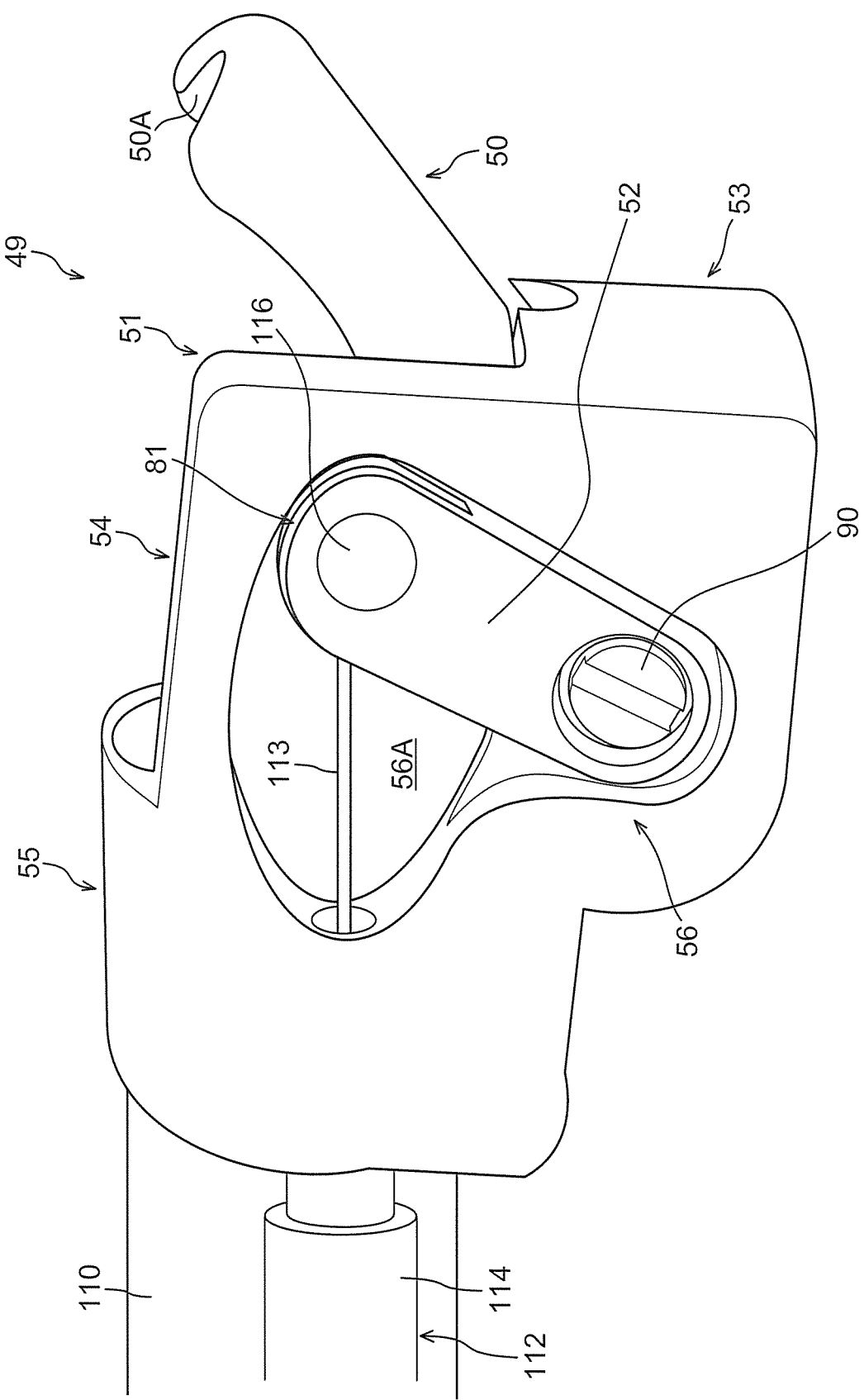
FIG. 5 is a perspective view illustrating the whole of the elevator assembly viewed from the right side.
Figure 6:
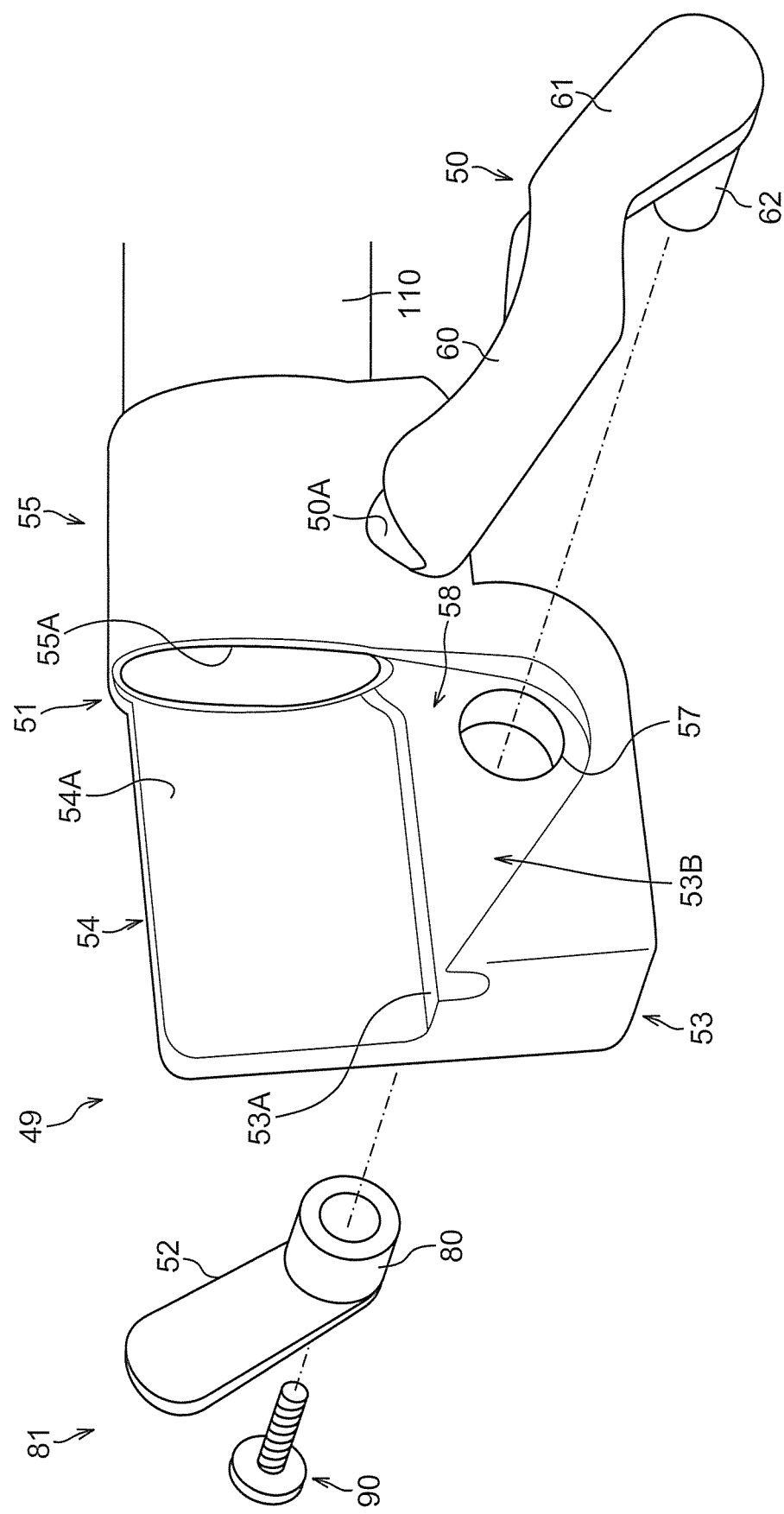
FIG. 6 is an exploded perspective view of the elevator assembly.
Figure 7:
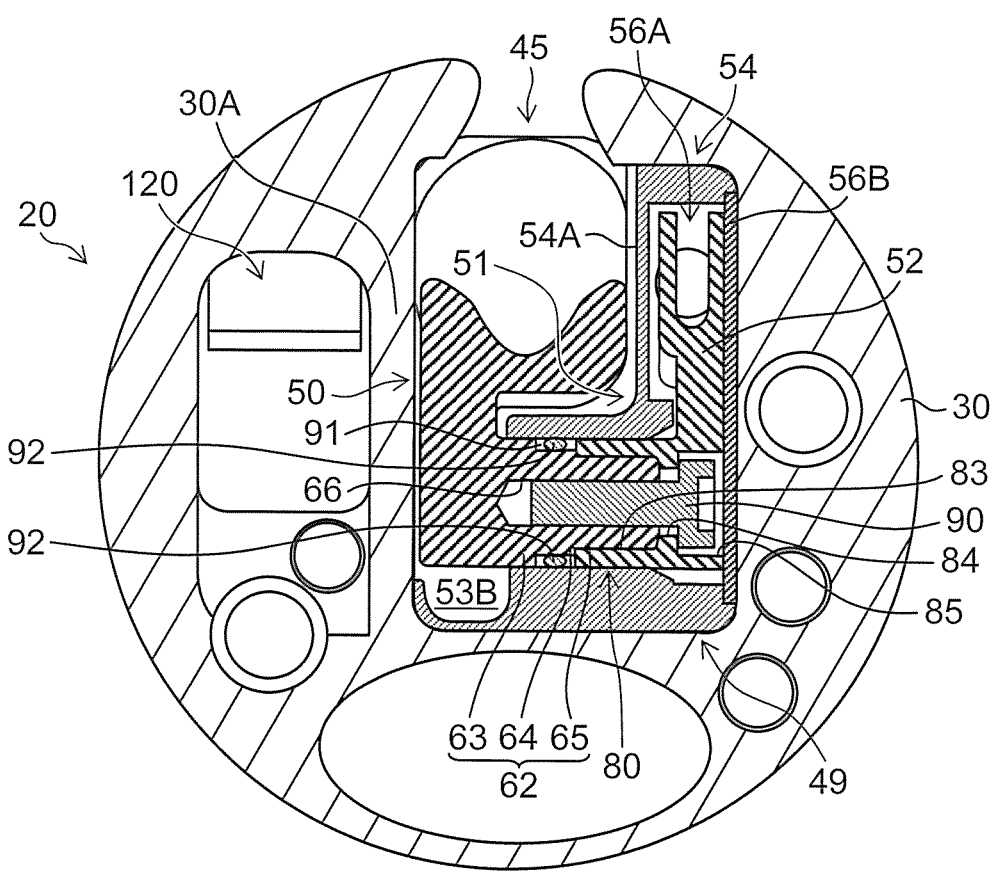
FIG. 7 is a sectional view viewed from a direction of arrows 7-7 in FIG. 3.

FIG. 4 is a perspective view illustrating the elevator assembly 49 viewed from the left side, FIG. 5 is a perspective view illustrating the whole of the elevator assembly 49 viewed from the right side, and FIG. 6 is an exploded perspective view of the elevator assembly 49. FIG. 7 is a sectional view viewed from a direction of arrows 7-7 in FIG. 3.

The elevator assembly 49 is integrally assembled as illustrated in FIGS. 4 and 5, and is accommodated and held in a predetermined accommodation section of the leading end body 30 to be fixed in the leading end section 20 as illustrated in FIG. 7.

As illustrated in FIGS. 4 to 7, the elevator assembly 49 is an elevator accommodation case, and includes an assembly body 51 that supports components, the elevator 50 supported by the assembly body 51, a raising lever 52 that allows the elevator 50 to rise and lie, and the like. In FIGS. 5 and 6, there is omitted a lid member 56B (refer to FIG. 7) with which a lever accommodation space 56A for accommodating the raising lever 52 is covered.

The assembly body 51, as illustrated in FIGS. 4 to 6, includes a base portion 53 that constitutes a lower portion of the assembly body 51, a partition 54 that constitutes an upper right portion of the assembly body 51 and serves as a partition wall between the elevator 50 and the raising lever 52, along with the base portion 53, and a treatment tool insertion portion 55 that constitutes a base end portion. While these components are integrally formed, separated components may be coupled to each other.

The base portion 53 is disposed below the elevator accommodation groove 45 with respect to an area of the elevator accommodation groove 45 in a state where the base portion 53 is accommodated in the leading end section 20 (the predetermined accommodation section of the leading end body 30) as the elevator assembly 49 as illustrated in FIGS. 2 and 3 (and FIG. 7).

In an area along a left face of the base portion 53, there is formed a recessed portion 53B for rotatable accommodating a support portion 61 of the elevator 50, the recessed portion 53B having an opened left face.

The partition 54 extends upward at a position along a right edge of a top face 53A of the base portion 53, and a left face 54A of the partition 54 constitutes a right wall face of the elevator accommodation groove 45.

The leading end body 30 (a partition wall 30A in FIG. 7) constitutes a left wall face of the elevator accommodation groove 45.

A lever accommodation section 56 is provided in an area along the base portion 53 and a right face of the partition 54 (refer to FIG. 5) to constitute the lever accommodation space 56A for rotatable accommodating the raising lever 52. The lever accommodation space 56A is provided with a cylindrical bearing hole 57 (refer to FIGS. 6 and 7) that penetrates to the recessed portion 53B of the base portion 53 to rotatable support the elevator 50 and the raising lever 52.

The treatment tool insertion portion 55 is connected to a base end side of each of the base portion 53 and the partition 54, and the treatment tool insertion portion 55 is disposed on a base end side of the elevator accommodation groove 45.

The treatment tool insertion portion 55 is provided with the treatment tool insertion hole 55A that opens toward the elevator accommodation groove 45. A pipe conduit member 110 constituting the treatment tool insertion channel is connected to a base end side of the treatment tool insertion portion 55 to allow the treatment tool insertion hole 55A to communicate with the treatment tool insertion channel.

The assembly body 51 includes a partition wall between the elevator 50 and the raising lever 52, the partition wall being composed of the base portion 53 and the partition 54, and the partition wall is provided with the bearing hole 57 for supporting the elevator 50 and the raising lever 52. The assembly body 51 also includes an open portion 58 opened toward an opposite side to the partition wall with respect to the elevator 50, and the open portion 58 is formed in an area including the elevator 50 as viewed from an axial direction of the bearing hole 57.

In FIG. 7, reference numeral 120 designates the imaging optical system constituting the optical observation section, and in the leading end section 20, the accommodation section for accommodating the elevator assembly 49 and an accommodation section for accommodating an imaging-system assembly in which components of the optical observation section are integrally assembled are separated by the partition wall 30A being a part of the leading end body 30. That is, when viewed from the leading end side along the longitudinal axis of the insertion section 10, the optical observation section is provided on a side where the open portion 58 of the elevator assembly 49 is provided. In a state where the elevator assembly 49 and the optical observation section are assembled in the leading end body 30, the optical observation section is provided in an area overlapping with at least an elevator rotation shaft portion 62 (described later) of the elevator 50 as viewed from an axial direction of the bearing hole 57.

The elevator 50 includes the elevator body 60 with a bilaterally symmetrical shape that is provided with the arc-like guide face 50A as described above, the support portion 61 that extends downward from a base end portion of the elevator body 60 and has a lateral width less than that of the elevator body 60, and the elevator rotation shaft portion 62 that is formed to project from the support portion 61 in a direction including a component of a direction orthogonal to the longitudinal axis of the insertion section 10, the elevator rotation shaft portion 62 being formed as a first rotation shaft portion.

The elevator rotation shaft portion 62 is inserted into the bearing hole 57 of the assembly body 51 from a recessed portion 53B side, and is rotatable supported in the bearing hole 57.

Accordingly, the support portion 61 of the elevator 50 is accommodated in the recessed portion 53B to be rotatable around an axis of the elevator rotation shaft portion 62, or around an axis of the bearing hole 57.

The elevator body 60 is accommodated at a position facing the treatment tool insertion hole 55A of the elevator accommodation groove 45 to be rotatable around the axis of the bearing hole 57, or to be able to rise and lie.

The raising lever 52 is formed in the shape of an elongated plate, and includes a lever rotation shaft portion 80 as a second rotation shaft portion that projects from one end side (base end side) of the raising lever 52 in a longitudinal direction. At the other end (leading end side), a wire coupling portion 81 to which an operation wire 113 is to be coupled is formed.

The lever rotation shaft portion 80 is inserted into the bearing hole 57 of the assembly body 51 from the lever accommodation space 56A side to be coupled to the elevator rotation shaft portion 62 of the elevator 50, and is fixed to the elevator rotation shaft portion 62 with a screw 90.

Accordingly, the lever rotation shaft portion 80 is formed coaxially with the elevator rotation shaft portion 62 to be coupled to the elevator rotation shaft portion 62, and thus the lever rotation shaft portion 80 is rotatably supported in the bearing hole 57 to be rotated integrally with the elevator rotation shaft portion 62. Details of a coupling mechanism of the elevator rotation shaft portion 62 and the lever rotation shaft portion 80 will be described later.

The raising lever 52 is accommodated in the lever accommodation space 56A to be rotatable around an axis of the lever rotation shaft portion 80, or around the axis of the bearing hole 57.

Meanwhile, as illustrated in FIG. 5, a control cable 112 including a guide tube 114 and the operation wire 113 inserted into the guide tube 114 is connected to a base end side of the lever accommodation section 56 in a base end portion of the treatment tool insertion portion 55 of the assembly body 51. One end (base end) of the operation wire 113 is coupled to the raising operation lever 24 of the operation section 11, and the operation wire 113 is pushed and pulled by operating the raising operation lever 24. The other end (leading end) of the operation wire 113 is inserted into the lever accommodation space 56A to be coupled to the wire coupling portion 81 of the raising lever 52 through a connection member 116.

According to the elevator assembly 49 described above, when the operation wire 113 is pushed or pulled by operating the raising operation lever 24, the raising lever 52 turns around the axis of the lever rotation shaft portion 80. Then, the elevator rotation shaft portion 62 turns in conjunction with turning of the raising lever 52 so that the elevator 50 rises and lies.

While an aspect of a transfer member for transferring displacement generated by the operation section 11 to the raising lever 52 is the operation wire 113 that is provided from the operation section 11 to the leading end body 30 through the insertion section 10, another aspect is available.

Subsequently, a coupling mechanism for coupling the elevator 50 and the raising lever 52 to each other (hereinafter, referred to as an elevator-lever coupling mechanism) will be described.

Figure 8:
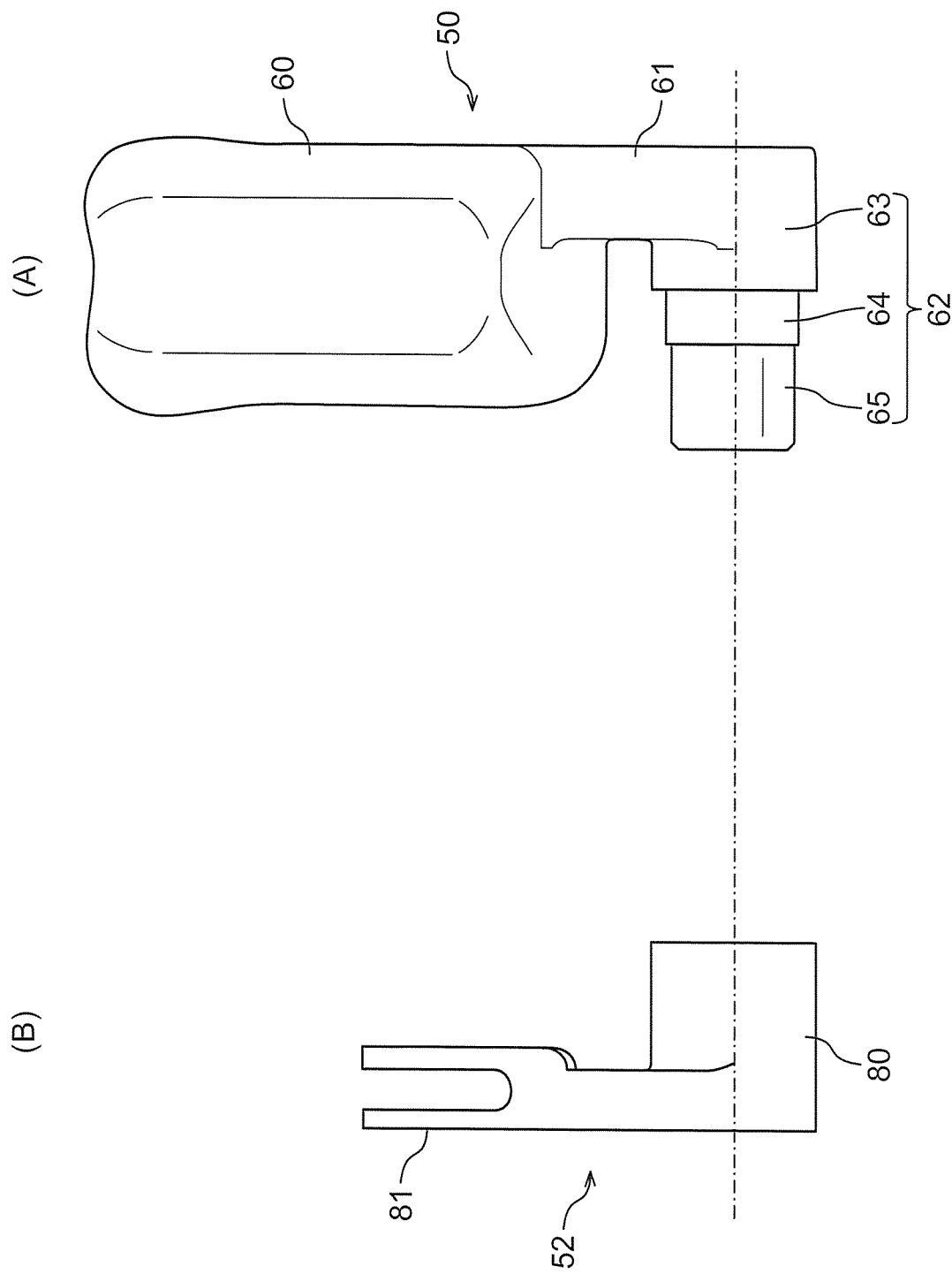
FIG. 8 is a front view of an elevator and a raising lever in a coupling mechanism that couples the elevator and the raising lever to each other.
Figure 9:
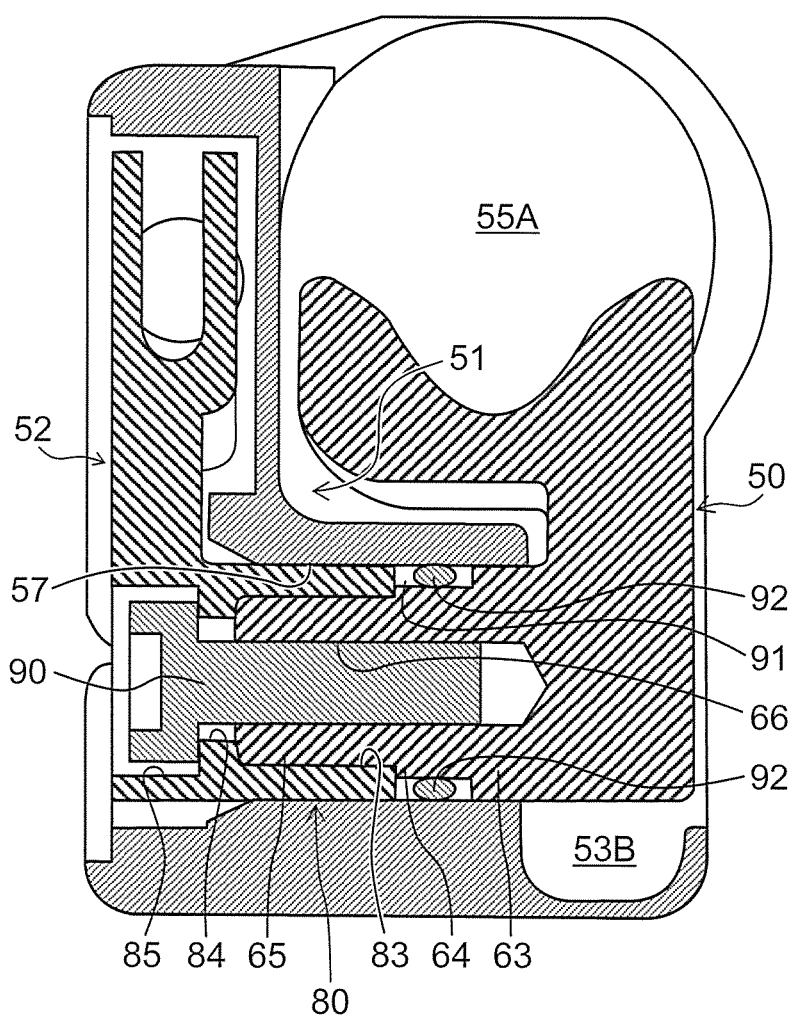
FIG. 9 is a sectional view of the coupling mechanism in the elevator assembly, taken along a plane including an axis of an elevator rotation shaft portion, the plane being perpendicular to an axis of an insertion section.

FIG. 8 is a front view of the elevator 50 and the raising lever 52 in the elevator-lever coupling mechanism of the present embodiment, and FIG. 9 is a sectional view of the elevator-lever coupling mechanism of the present embodiment in the elevator assembly 49, taken along a plane including the axis of the elevator rotation shaft portion 62 (bearing hole 57), the plane being perpendicular to an axis of the leading end section 20 (longitudinal axis of the insertion section 10).

As illustrated in the (A) portion of FIGS. 8 and 9, the elevator rotation shaft portion 62 of the elevator 50 projects from the support portion 61, and includes a large diameter portion 63, a small diameter portion 64, and a rotation regulation portion 65 in order from the support portion 61.

The large diameter portion 63 is formed like a column, and has an outer diameter that is substantially equal to an inner diameter of the bearing hole 57 of the assembly body 51.

The small diameter portion 64 is provided adjacent to the large diameter portion 63 on a side facing the raising lever 52, and is formed like a column. In addition, the small diameter portion 64 has an outer diameter smaller than the outer diameter of the large diameter portion 63, and is provided with a seal member 92 (refer to FIG. 9) that is fit around the small diameter portion 64.

The rotation regulation portion 65 extends from the small diameter portion 64, and is formed like a quadrangular prism. In addition, the rotation regulation portion 65 like a quadrangular prism has a diagonal length (diameter of a circumscribed cylinder) smaller than the outer diameter of the small diameter portion 64.

In addition, a screw hole 66 (refer to FIG. 9) is formed from a leading end face of the rotation regulation portion 65 toward an opposite face thereof, along an axis of the elevator rotation shaft portion 62.

Meanwhile, as illustrated in the (B) portion of FIGS. 8 and 9, the lever rotation shaft portion 80 of the raising lever 52 is formed like a column, and has an outer diameter that is substantially equal to the inner diameter of the bearing hole 57 of the assembly body 51.

A fitting hole 83 like a quadrangular prism is formed in a leading end face of the lever rotation shaft portion 80 toward an opposite face thereof along the axis of the lever rotation shaft portion 80 so that the rotation regulation portion 65 of the elevator rotation shaft portion 62 can be fitted into the fitting hole 83 substantially without a gap.

The fitting hole 83 has an axial length that is substantially equal to an axial length of the rotation regulation portion 65.

In addition, a screw insertion hole 84 having a diameter smaller than a diagonal length of the fitting hole 83 is formed in a bottom face of the fitting hole 83 toward a face opposite to the bottom face, along the axis of the lever rotation shaft portion 80. Then, a counterbore hole 85 having an inner diameter larger than an inner diameter of the screw insertion hole 84 is formed while communicating with the screw insertion hole 84, and penetrates to a face opposite to the leading end face of the lever rotation shaft portion 80.

The elevator 50 and the raising lever 52 in the elevator-lever coupling mechanism of a first embodiment described above allow the elevator rotation shaft portion 62 of the elevator 50 to be inserted from the recessed portion 53B in the assembly body 51 of the elevator assembly 49, and allow the lever rotation shaft portion 80 of the raising lever 52 to be inserted into the bearing hole 57 from the lever accommodation space 56A opposite to the recessed portion 53B.

The rotation regulation portion 65 of the elevator rotation shaft portion 62 is fitted into the fitting hole 83 of the lever rotation shaft portion 80, and the elevator rotation shaft portion 62 and the lever rotation shaft portion 80 are coupled to each other at a predetermined rotation angle. Then, the screw 90 with a head part is inserted into the counterbore hole 85 of the raising lever 52 to be screwed into the screw hole 66 of the elevator rotation shaft portion 62.

As a result, the elevator rotation shaft portion 62 and the lever rotation shaft portion 80 are coupled to each other.

In a state where the elevator rotation shaft portion 62 and the lever rotation shaft portion 80 are coupled to each other as described above, the elevator rotation shaft portion 62 and the lever rotation shaft portion 80 are fixed while the leading end face of the lever rotation shaft portion 80 is in contact with a stepped face formed in a step between the small diameter portion 64 and the rotation regulation portion 65 of the elevator rotation shaft portion 62. Then, a seal groove 91 along a circumferential direction, as a position regulation groove of the seal member 92, is formed between a first regulation face that is a stepped face formed in a step between the large diameter portion 63 and the small diameter portion 64 of the elevator rotation shaft portion 62, and a second regulation face that is the leading end face of the lever rotation shaft portion 80 and faces the first regulation face. The first regulation face and the second regulation face each have a normal direction that is an axial direction of the elevator rotation shaft portion 62.

Meanwhile, before the elevator rotation shaft portion 62 is inserted into the bearing hole 57 of the assembly body 51, the seal member 92 such as an O-ring is fitted around an outer peripheral surface of the small diameter portion 64. Thus, when the elevator rotation shaft portion 62 is inserted into the bearing hole 57 to couple the elevator rotation shaft portion 62 and the lever rotation shaft portion 80 to each other, the seal groove 91 serves as a positioning portion for positioning the seal member 92 in the axial direction of the bearing hole 57 to allow the seal member 92 to be disposed in the seal groove 91 while the seal member 92 is positioned. Then, the seal member 92 is brought into close contact with an internal wall face of the bearing hole 57.

Accordingly, the lever accommodation space 56A of the lever accommodation section 56 is airtightly sealed from the elevator accommodation groove 45 to prevent blood, water, or the like, from entering the lever accommodation space 56A from the elevator accommodation groove 45.

In addition, since a coupled position of the elevator rotation shaft portion 62 and the lever rotation shaft portion 80 is positioned closer to the raising lever 52 than the seal member 92, blood, water, or the like cannot enter the lever accommodation space 56A from the elevator accommodation groove 45 or a gap in a coupling portion of the elevator rotation shaft portion 62 and the lever rotation shaft portion 80. Further, there is no coupling portion between members through which blood, water, or the like enters, in a portion closer to the elevator accommodation groove 45 than the seal member 92.

The elevator accommodation groove 45 has the open portion 58 on a side opposite to the partition wall of the assembly body 51 with respect to the elevator 50, and thus when the elevator assembly 49 is assembled, the elevator 50 can be inserted into the elevator accommodation groove 45 from the open portion 58 to be disposed, and the elevator rotation shaft portion 62 can be inserted into the bearing hole 57 from the open portion 58 to be disposed. Thus, no extra space is needed to dispose the elevator 50 in the elevator accommodation groove 45, and a width of the elevator accommodation groove 45 can be substantially equal to a width of the elevator body 60, whereby the leading end section 20 is prevented from increasing in size.

Instead of the seal groove 91 of the present embodiment, as the seal groove for disposing the seal member 92, for example, a groove in a circumferential direction may be formed in the elevator rotation shaft portion 62 or the lever rotation shaft portion 80, or a groove in a circumferential direction is formed in the internal wall face of the bearing hole 57, and the groove may serve as a seal groove (position regulation groove).

Unfortunately, since it is not easy to form a groove in the circumferential direction in the elevator rotation shaft portion 62 formed integrally with the elevator body 60 and the like, or in the bearing hole 57, forming the seal groove 91 by combination with lever rotation shaft portion 80 like the present embodiment enables the elevator 50 and the like to be easily worked.

While the raising lever 52 has the lever rotation shaft portion 80 as the second rotation shaft portion in the elevator-lever coupling mechanism, the raising lever 52 may not have the lever rotation shaft portion 80. In this case, the elevator rotation shaft portion 62 of the elevator 50 is configured to be directly coupled to a body portion (plate-shaped portion) of the raising lever 52.

The elevator-lever coupling mechanism is not limited to the present embodiment, and can use appropriate structure.

Next, the elevator 50 and its peripheral components for improving easiness of cleaning operation of the elevator 50 will be described in detail.

Figure 10:
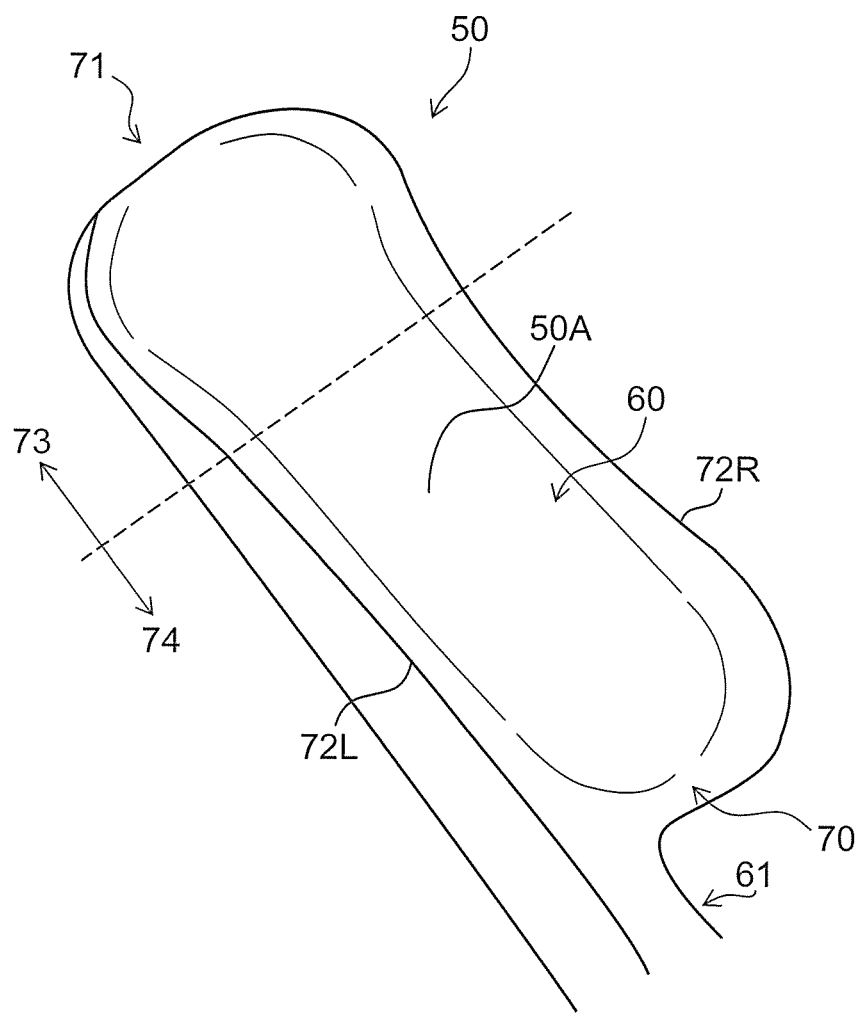
FIG. 10 is an enlarged perspective view illustrating an elevator body.
Figure 11:
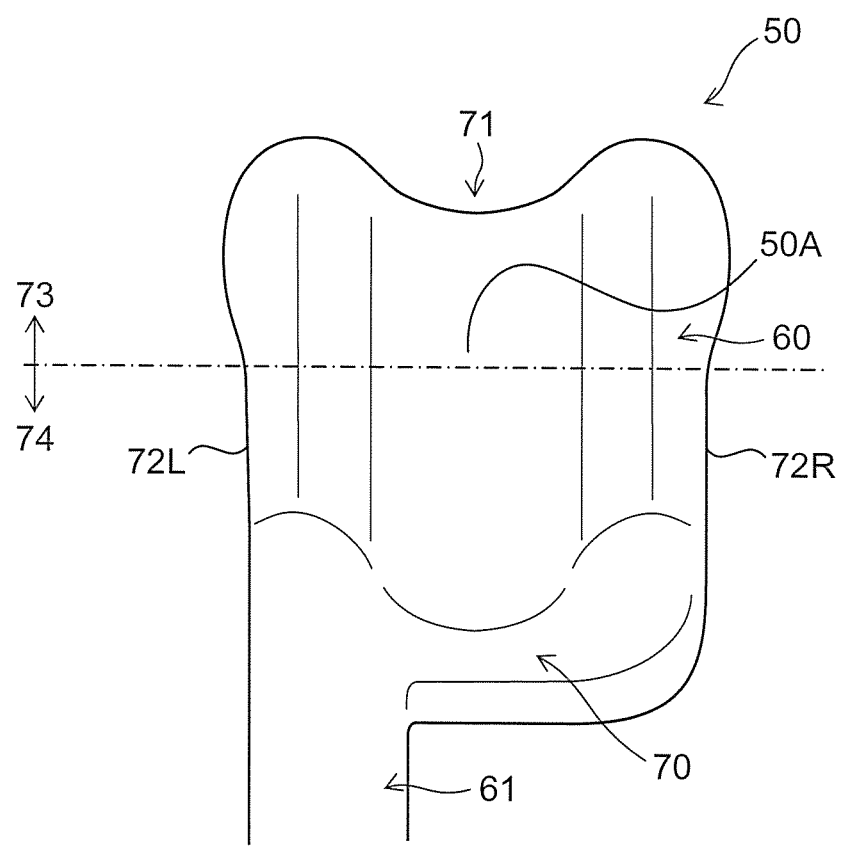
FIG. 11 is an enlarged front view illustrating the elevator body.

FIGS. 10 and 11 are enlarged perspective and front views, respectively, illustrating the elevator body 60 of the elevator 50. The front view of FIG. 11 illustrates the elevator body 60 viewed from a direction in which the elevator body 60 is the base end of the leading end section 20.

As illustrated in these drawings, the elevator body 60 has a bilaterally symmetrical shape, and includes a proximal end portion 70, a distal end portion 71 that has a distance from the axis of the elevator rotation shaft portion 62 (hereinafter referred to as a rotation axis of the elevator 50, or simply a rotation axis) in a radial direction of the rotation axis, the distance being more than a distance therefrom to the proximal end portion 70, the guide face 50A provided between the proximal end portion 70 and the distal end portion 71, and elevator side faces 72R and 72L each of which is adjacent to the guide face 50A, and has a normal direction to be a direction including a component of a direction of the rotation axis.

The elevator body 60 also includes a wide body portion 73 on its distal end portion 71 side, and a narrow body portion 74 that is formed closer to the proximal end portion 70 than the wide body portion 73, and has a width in the direction of the rotation axis less than that of the wide body portion 73.

In addition, the wide body portion 73 of the elevator body 60 has rounded cross sectional and longitudinal sectional shapes with respect to the direction of the rotation axis. In this case, the entire section may be rounded, or may have a shape chamfered to a level without an acute edge. Such a shape may not damage the inside of the body regardless of a position of the elevator 50.

Figure 12:
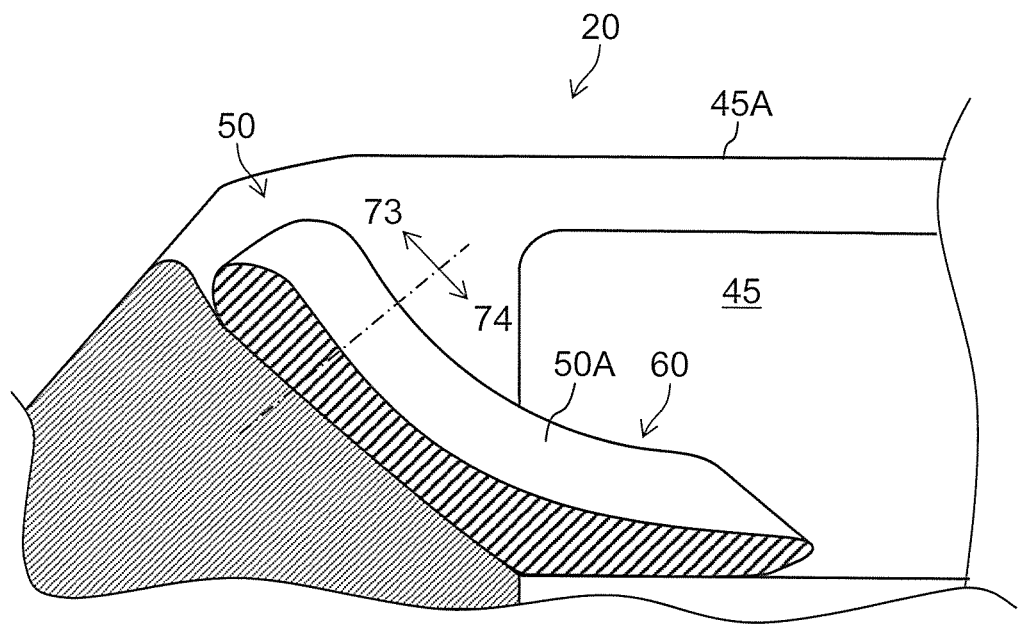
FIG. 12 is a sectional view of the elevator rotation shaft portion in the leading end section with respect to a direction orthogonal to a direction of the axis of the elevator rotation shaft portion in a state where the elevator is lying.
Figure 13:
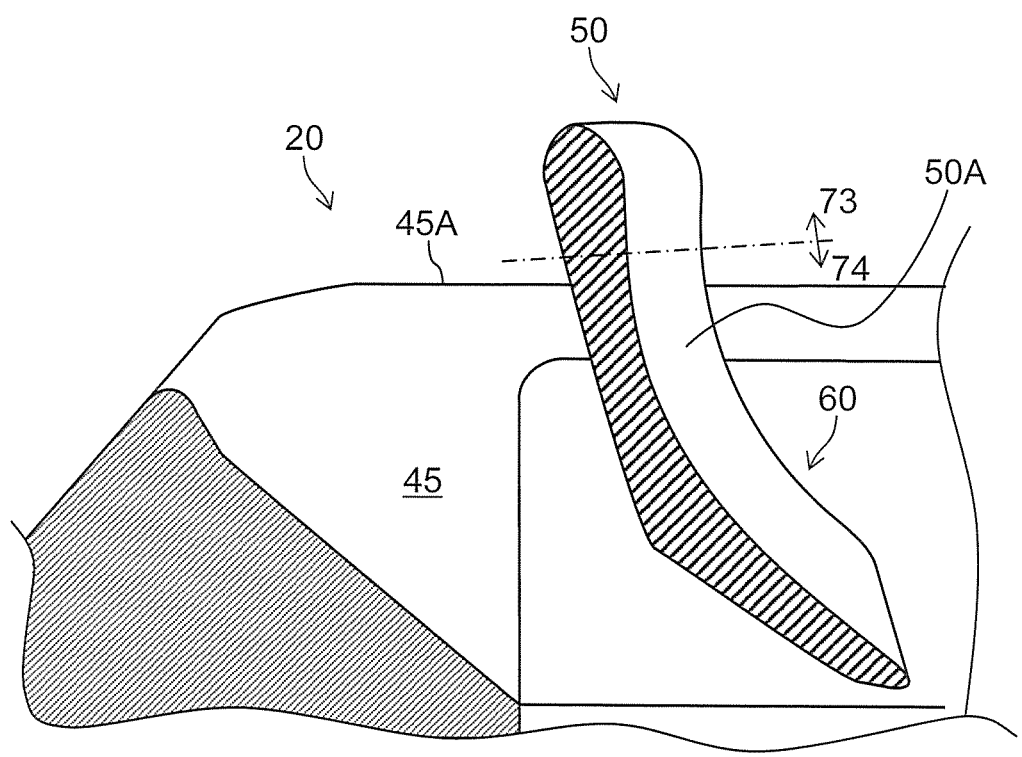
FIG. 13 is a sectional view of the elevator rotation shaft portion in the leading end section with respect to the direction orthogonal to the direction of the axis of the elevator rotation shaft portion in a state where the elevator rises.

FIGS. 12 and 13 each are a sectional view of the leading end section 20 with respect to a direction orthogonal to the direction of the rotation axis, the sectional view being taken along a line passing through the center of the elevator body 60 in its width direction (the direction of the rotation axis). FIG. 12 illustrates a state where the elevator 50 is lying, and FIG. 13 illustrates a state where the elevator 50 rises most.

Figure 14:
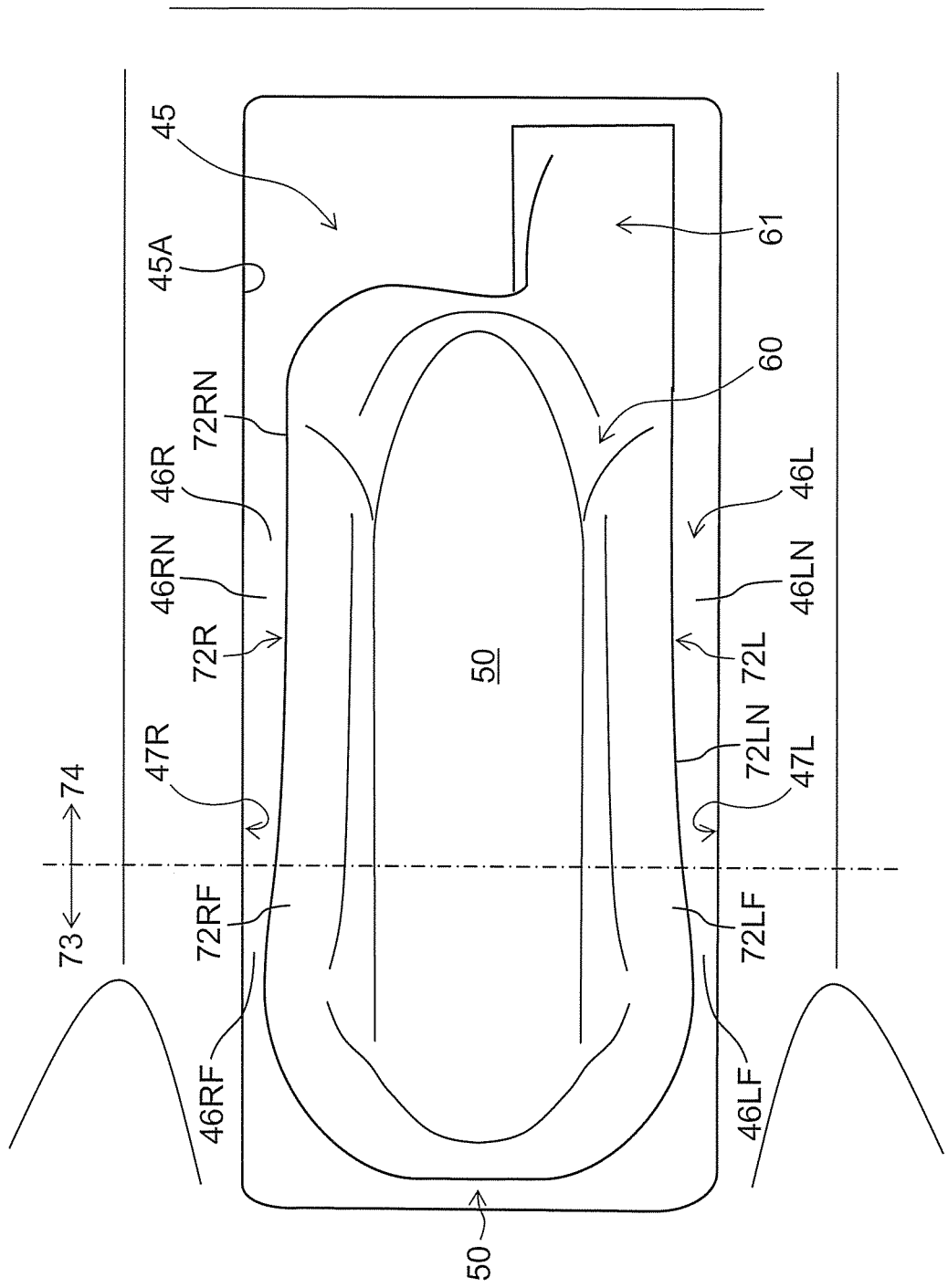
FIG. 14 is a top view illustrating a peripheral portion of the elevator in the leading end section in a state where the elevator is lying.
Figure 15:
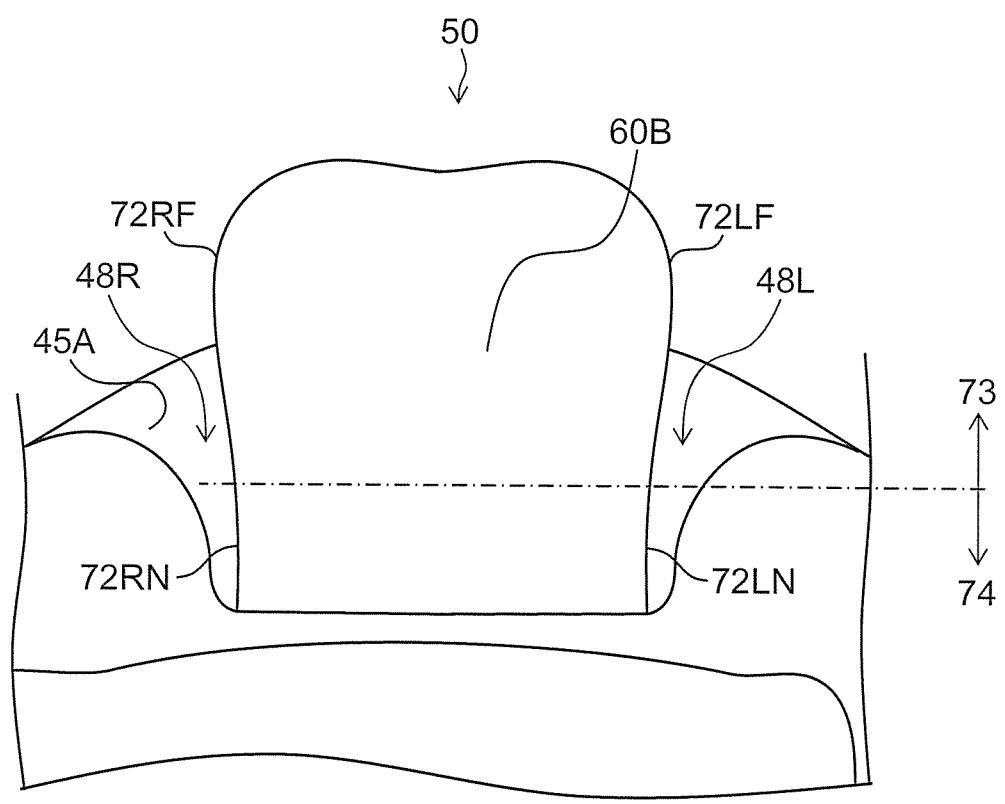
FIG. 15 is a front view illustrating the peripheral portion of the elevator in the leading end section in a state where the elevator rises most.

FIG. 14 is a top view illustrating a peripheral portion of the elevator 50 in the leading end section 20 in a state where the elevator 50 is lying, and FIG. 15 is a front view illustrating the peripheral portion of the elevator 50 in the leading end section 20 in a state where the elevator 50 rises most. A state where the elevator 50 rises as illustrated in FIGS. 13 and 15 represents the state where the elevator 50 rises most, however, the elevator 50 may not necessarily rise most.

As illustrated in FIG. 14, the elevator accommodation groove 45 includes the elevator side faces 72R and 72L, and the elevator accommodation groove side faces 47R and 47L facing each other across the gap portions 46R and 46L, as right and left side wall faces.

In a state where the elevator 50 is lying as illustrated in FIGS. 12 and 14, the whole of the elevator body 60 is accommodated in the elevator accommodation groove 45. In the present embodiment, while the elevator accommodation groove side faces 47R and 47L are formed along a plane, the elevator body 60 includes the wide body portion 73 and the narrow body portion 74. Thus, in a state where the elevator 50 is lying, the gap portions 46R and 46L respectively include: narrow gap portions 46RF and 46LF formed between distal end portion side faces 72RF and 72LF in the elevator side faces 72R and 72L, positioned on the distal end portion 71 side, and the elevator accommodation groove side faces 47R and 47L; and wide gap portions 46RN and 46LN formed between proximal end portion side faces 72RN and 72LN in the elevator side faces 72R and 72L, positioned closer to the proximal end portion 70 than the distal end portion side faces 72RF and 72LF, and the elevator accommodation groove side faces 47R and 47L, the wide gap portions 46RN and 46LN each having a width in the direction of the rotation axis more than that of each of the narrow gap portions 46RF and 46LF.

Thus, a treatment tool led to the elevator accommodation groove 45 from the treatment tool insertion hole 55A of the treatment tool leading section 41 is prevented from dropping into the gap portions 46R and 46L each in a side of the elevator body 60 by the wide body portion 73 of the elevator body 60, or by the narrow gap portions 46RF and 46LF.

Meanwhile, in a state where the elevator 50 rises most as illustrated in FIGS. 13 and 15, the wide body portion 73 of the elevator body 60 projects outside through the opening 45A of the elevator accommodation groove 45. Since the wide body portion 73 of the elevator body 60 has a rounded shape, no special attention is needed even if the wide body portion 73 projects outside through the opening 45A.

The elevator accommodation groove 45 includes leading portions 48R and 48L that are formed in a rounded shape in cross section by chamfering an edge of the opening 45A of the elevator accommodation groove 45. The leading portions 48R and 48L each increase in width in the direction of the rotation axis toward the opening 45A.

Since a size of a chamfer of each of the leading portions 48R and 48L is twice or more a wire diameter of each of bristles of a cleaning brush to be used for cleaning the elevator 50, the bristles of the cleaning brush are led to a gap between the elevator body 60 and each of the elevator accommodation groove side faces 47R and 47L.

Since a back face 60B opposite to the guide face 50A of the elevator body 60 has an rounded shape in longitudinal section with respect to the direction of the rotation axis, the bristles of the cleaning brush are led to a gap between the back face 60B and each of the elevator accommodation groove side faces 47R and 47L.

Thus, time and effort required for cleaning operation of the elevator 50 is reduced when the elevator 50 (and its peripheral portion) is cleaned with a cleaning brush, because raising the elevator 50 exposes the side faces (distal end portion side faces 72RF and 72LF) of the wide body portion 73 of the elevator body 60, and bristles of the cleaning brush is easily led into a gap between the elevator body 60 and each of the elevator accommodation groove side faces 47R and 47L, the gap being difficult to be cleaned.

In the embodiment describe above, while the narrow gap portion 46RF and 46LF, and the wide gap portions 46RN and 46LN are acquired by using the wide body portion 73 and the narrow body portion 74 of the elevator body 60 in a state where the elevator 50 is lying (refer to FIG. 14), structure is not limited to the above.

For example, as illustrated in FIG. 16, while the elevator side faces 72R and 72L is formed along a plane, the elevator accommodation groove 45 may include a narrow groove 200 provided on a distal end portion 71 side of the elevator 50, and a wide groove 202 that is provided closer to the proximal end portion 70 than the narrow groove 200, and has a width in the direction of the rotation axis more than that of the narrow groove 200, in a state where the elevator 50 is lying.

Accordingly, as with the embodiment described above, the gap portions 46R and 46L respectively include the narrow gap portions 46RF and 46LF on their leading end sides, and the wide gap portions 46RN and 46LN on their base end sides. The narrow groove 200 is adjacent to the narrow gap portions 46RF and 46LF, and the wide groove 202 is adjacent to the wide gap portions 46RN and 46LN.

In the embodiment described above, while there is described the case where the present invention is applied to the ultrasound endoscope 2 including the ultrasound observation section 100 and the elevator 50 in the leading end section 20, the present invention can be applied to even an endoscope without an ultrasound observation section, such as a side-viewing endoscope including an elevator.

What is claimed is:

1. An endoscope comprising:
an insertion section having a leading end and a base end;
an operation section provided at the base end of the insertion section;
a leading end body provided at the leading end of the insertion section;
an elevator accommodation groove provided in the leading end body, the groove having an opening located at a top surface of the leading end body;
a treatment tool insertion channel provided in the insertion section, the channel communicating with the elevator accommodation groove; and
a treatment tool elevator provided in the elevator accommodation groove to be rotatable around a rotation axis, the rotation axis being in a direction including a component of a direction orthogonal to a longitudinal axis of the insertion section, the treatment tool elevator guiding a treatment tool led through the treatment tool insertion channel,
the treatment tool elevator including:
a proximal end portion;
a distal end portion with a radial distance from the rotation axis more than a radial distance to the proximal end portion from the rotation axis;
a treatment tool guiding face provided between the proximal end portion and the distal end portion; and
an elevator side face adjacent to the treatment tool guiding face, the side face having a normal direction including an axial component of the rotation axis,
the elevator accommodation groove including:
an elevator accommodation groove side face facing the elevator side face across a gap portion,
the gap portion, in a state where the treatment tool elevator is lying, including:
a narrow gap portion formed between a distal end portion side face, which is positioned at the distal end portion in the elevator side face, and the elevator accommodation groove side face; and
a wide gap portion formed between a proximal end portion side face, which is closer to the proximal end portion than the distal end portion side face in the elevator side face, and the elevator accommodation groove side face, the wide gap portion being wider axially than the narrow gap portion,
wherein in a state where the treatment tool elevator rises, the distal end portion side face is completely exposed outside from the opening of the elevator accommodation groove,
wherein the treatment tool elevator includes a wide body portion that projects outside from the opening of the elevator accommodation groove when the treatment tool elevator provided on the distal end portion side rises, and a narrow body portion that is provided closer to the proximal end portion than the wide body portion, and is narrower axially than the wide body portion,
wherein along the longitudinal axis of the insertion section, an entire length of the narrow body portion is longer than an entire length of the wide body portion, and a width of the narrow body portion decreases gradually from a junction of the wide body portion and the narrow body portion toward the proximal end portion, wherein in the state where the treatment tool elevator rises, a part of the narrow body portion projects outside from the opening of the elevator accommodation groove, wherein the elevator side face has a first elevator side face and a second elevator side face opposite to each other, and the elevator accommodation groove side face has a first elevator accommodation groove side face and a second elevator accommodation groove side face opposite to each other, wherein in the state where the treatment tool elevator is lying, the first elevator side face faces the first elevator accommodation groove side face, the second elevator side face faces the second elevator accommodation groove side face, and the gap portion between the first elevator side face and the first elevator accommodation groove side face and the gap portion between the second elevator side face and the second elevator accommodation groove side face are symmetrical with respect to a central axis in the longitudinal axis of the insertion section.

2. The endoscope according to claim 1, wherein the wide body portion has a longitudinal section with a rounded shape with respect to an axial direction of the wide body portion.

3. The endoscope according to claim 2, wherein the wide body portion has a cross section with a rounded shape with respect to the axial direction of the wide body portion.

4. The endoscope according to claim 3, wherein in the state where the treatment tool elevator is lying, the elevator accommodation groove includes a narrow groove on a side of the distal end portion, and a wide groove that is provided closer to the proximal end portion than the narrow groove and is wider axially than the narrow groove.

5. The endoscope according to claim 3, wherein the elevator accommodation groove includes a leading portion which is a gap between a side face of the treatment tool elevator and an edge of the opening, and a width of the gap increases toward the top surface of the leading end body.

6. The endoscope according to claim 2, wherein in the state where the treatment tool elevator is lying, the elevator accommodation groove includes a narrow groove on a side of the distal end portion, and a wide groove that is provided closer to the proximal end portion than the narrow groove and is wider axially than the narrow groove.

7. The endoscope according to claim 2, wherein the elevator accommodation groove includes a leading portion which is a gap between a side face of the treatment tool elevator and an edge of the opening, and a width of the gap increases toward the top surface of the leading end body.

8. The endoscope according to claim 1, wherein the wide body portion has a cross section with a rounded shape with respect to an axial direction of the wide body portion.

9. The endoscope according to claim 8, wherein in the state where the treatment tool elevator is lying, the elevator accommodation groove includes a narrow groove on a side of the distal end portion, and a wide groove that is provided closer to the proximal end portion than the narrow groove and is wider axially than the narrow groove.

10. The endoscope according to claim 8, wherein the elevator accommodation groove includes a leading portion which is a gap between a side face of the treatment tool elevator and an edge of the opening, and a width of the gap increases toward the top surface of the leading end body.

11. The endoscope according to claim 1, wherein in the state where the treatment tool elevator is lying, the elevator accommodation groove includes a narrow groove on a side of the distal end portion, and a wide groove that is provided closer to the proximal end portion than the narrow groove and is wider axially than the narrow groove.

12. The endoscope according to claim 1, wherein the elevator accommodation groove includes a leading portion which is a gap between a side face of the treatment tool elevator and an edge of the opening, and a width of the gap increases toward the top surface of the leading end body.

13. The endoscope according to claim 12, wherein the edge of the opening of the elevator accommodation groove has a cross section with a rounded shape perpendicular to the longitudinal axis of the insertion section.

14. The endoscope according to claim 1, wherein a section of the top surface of the leading end body having the elevator accommodation groove inclines relative to the longitudinal axis of the insertion section.

15. The endoscope according to claim 1, wherein a back face of the treatment tool elevator, the back face being opposite to the treatment tool guiding face, has a longitudinal section with a rounded shape with respect to an axial direction of the back face.

16. The endoscope according to claim 1, comprising a raising lever that is provided in the leading end body and is coupled to the treatment tool elevator to turn the treatment tool elevator around the rotation axis, and an operation wire that is provided from the operation section to the leading end body through the insertion section and transfers displacement generated in the operation section to the raising lever.

17. An endoscope comprising:
an insertion section having a leading end and a base end;
an operation section provided at the base end of the insertion section;
a leading end body provided at the leading end of the insertion section;
an elevator accommodation groove provided in the leading end body, the groove having an opening located at a top surface of the leading end body;
a treatment tool insertion channel provided in the insertion section, the channel communicating with the elevator accommodation groove; and
a treatment tool elevator provided in the elevator accommodation groove to be rotatable around a rotation axis, the rotation axis being in a direction including a component of a direction orthogonal to a longitudinal axis of the insertion section, the treatment tool elevator guiding a treatment tool led through the treatment tool insertion channel,
the treatment tool elevator including:
a proximal end portion;

a distal end portion with a radial distance from the rotation axis more than a radial distance to the proximal end portion from the rotation axis;

a treatment tool guiding face provided between the proximal end portion and the distal end portion; and an elevator side face adjacent to the treatment tool guiding face, the side face having a normal direction including an axial component of the rotation axis, the elevator accommodation groove including:

an elevator accommodation groove side face facing the elevator side face across a gap portion, the gap portion, a state where the treatment tool elevator is lying, including:

a narrow gap portion formed between a distal end portion side face, which is positioned at the distal end portion in the elevator side face, and the elevator accommodation groove side face; and a wide gap portion formed between a proximal end portion side face, which is closer to the proximal end portion than the distal end portion side face in the elevator side face, and the elevator accommodation groove side face, the wide gap portion being wider axially than the narrow gap portion, wherein in a state where the treatment tool elevator rises, the distal end portion side face projects outside from the opening of the elevator accommodation groove, wherein the elevator accommodation groove includes a leading portion which is a gap between a side face of the treatment tool elevator and an edge of the opening, and a width of the gap increases toward the top surface of the leading end body, wherein the treatment tool elevator includes a wide body portion that projects outside from the opening of the elevator accommodation groove when the treatment tool elevator provided on the distal end portion side rises, and a narrow body portion that is provided closer to the proximal end portion than the wide body portion, and is narrower axially than the wide body portion, wherein along the longitudinal axis of the insertion section, an entire length of the narrow body portion is longer than an entire length of the wide body portion, and a width of the narrow body portion decreases gradually from a junction of the wide body portion and the narrow body portion toward the proximal end portion, wherein in the state where the treatment tool elevator rises, a part of the narrow body portion projects outside from the opening of the elevator accommodation groove, wherein the elevator side face has a first elevator side face and a second elevator side face opposite to each other, and the elevator accommodation groove side face has a first elevator accommodation groove side face and a second elevator accommodation groove side face opposite to each other, wherein in the state where the treatment tool elevator is lying, the first elevator side face faces the first elevator accommodation groove side face, the second elevator side face faces the second elevator accommodation groove side face, and the gap portion between the first elevator side face and the first elevator accommodation groove side face and the gap portion between the second elevator side face and the second elevator accommodation groove side face are symmetrical with respect to a central axis in the longitudinal axis of the insertion section.

18. The endoscope according to claim 17, wherein the wide body portion has a longitudinal section with a rounded shape with respect to an axial direction of the wide body portion.

19. The endoscope according to claim 18, wherein the wide body portion has a cross section with a rounded shape with respect to the axial direction of the wide body portion.

20. The endoscope according to claim 19, wherein in the state where the treatment tool elevator is lying, the elevator accommodation groove includes a narrow groove on a side of the distal end portion, and a wide groove that is provided closer to the proximal end portion than the narrow groove and is wider axially than the narrow groove.

21. The endoscope according to claim 18, wherein in the state where the treatment tool elevator is lying, the elevator accommodation groove includes a narrow groove on a side of the distal end portion, and a wide groove that is provided closer to the proximal end portion than the narrow groove and is wider axially than the narrow groove.

22. The endoscope according to claim 17, wherein the wide body portion has a cross section with a rounded shape with respect to an axial direction of the wide body portion.

23. The endoscope according to claim 22, wherein in the state where the treatment tool elevator is lying, the elevator accommodation groove includes a narrow groove on a side of the distal end portion, and a wide groove that is provided closer to the proximal end portion than the narrow groove and is wider axially than the narrow groove.

24. The endoscope according to claim 17, wherein in the state where the treatment tool elevator is lying, the elevator accommodation groove includes a narrow groove on a side of the distal end portion, and a wide groove that is provided closer to the proximal end portion than the narrow groove and is wider axially than the narrow groove.

25. The endoscope according to claim 17, wherein the edge of the opening of the elevator accommodation groove has a cross section with a rounded shape perpendicular to the longitudinal axis of the insertion section.

26. The endoscope according to claim 17, wherein a back face of the treatment tool elevator, the back face being opposite to the treatment tool guiding face, has a longitudinal section with a rounded shape with respect to an axial direction of the back face.

27. The endoscope according to claim 17, comprising a raising lever that is provided in the leading end body and is coupled to the treatment tool elevator to turn the treatment tool elevator around the rotation axis, and an operation wire that is provided from the operation section to the leading end body through the insertion section and transfers displacement generated in the operation section to the raising lever.

* * * * *